US011083373B1

(12) United States Patent
Reed et al.

(10) Patent No.: US 11,083,373 B1
(45) Date of Patent: Aug. 10, 2021

(54) SYSTEMS AND METHODS FOR NEUROLOGIC VIBRATORY SENSE EVALUATION

(71) Applicant: UNIVERSITY OF SOUTH FLORIDA, Tampa, FL (US)

(72) Inventors: Kyle Brandon Reed, Tampa, FL (US); Theresa Ann Zesiewicz, Oldsmar, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 117 days.

(21) Appl. No.: 16/359,343

(22) Filed: Mar. 20, 2019

(51) Int. Cl.
*A61B 5/00* (2006.01)

(52) U.S. Cl.
CPC .......... *A61B 5/0051* (2013.01); *A61B 5/4041* (2013.01); *A61B 5/6804* (2013.01); *A61B 5/4827* (2013.01)

(58) Field of Classification Search
CPC ... A61B 5/0051; A61B 5/4041; A61B 5/6804; A61B 5/4827
See application file for complete search history.

(56) References Cited

U.S. PATENT DOCUMENTS

| | | | |
|---|---|---|---|
| 5,002,065 A | 3/1991 | LaCourse | |
| 8,579,830 B2 * | 11/2013 | Golosarsky | A61B 5/483 600/557 |
| 8,684,945 B2 * | 4/2014 | O'Brien | A61B 5/4827 600/552 |
| 8,795,190 B2 * | 8/2014 | O'Brien | A61B 5/0051 600/552 |
| 9,610,039 B2 * | 4/2017 | Golosarsky | A61B 5/4827 |
| 9,687,404 B2 * | 6/2017 | Cheatham, III | A61F 5/0109 |
| 10,668,305 B2 * | 6/2020 | Cheatham, III | A61N 1/36021 |
| 2012/0046580 A1 | 2/2012 | O'Brien | |
| 2013/0066216 A1 * | 3/2013 | Park | A61B 5/6804 600/483 |
| 2014/0148727 A1 | 1/2014 | O'Brien | |
| 2018/0153406 A1 * | 6/2018 | Hickish | A61B 5/4041 |

OTHER PUBLICATIONS

O'Brien, Todd, and Joseph Karem. "Relative sensory sparing in the diabetic foot implied through vibration testing." Diabetic foot & ankle 4.1 (2013): 21278.
O'Brien, Todd, and Joseph Karem. "An initial evaluation of a proof-of-concept 128-Hz electronic tuning fork in the detection of peripheral neuropathy." Journal of the American Podiatric Medical Association 104.2 (2014): 134-140.
Bracewell, N., et al. "Clinical evaluation of a new device in the assessment of peripheral sensory neuropathy in diabetes." Diabetic Medicine 29.12 (2012): 1553-1555.

* cited by examiner

*Primary Examiner* — Steven O Douglas

(57) ABSTRACT

In one embodiment, a system for neurologic vibratory sense evaluation includes a vibration article configured to attach to a body part of a patient under evaluation, the vibration article comprising a vibration element configured to vibrate against the body part, a control module configured to control an amplitude of vibrations generated by the vibration element, and a patient input device configured to enable a patient to start and stop an evaluation session, wherein starting the session in a first mode of operation causes the vibration element to initially vibrate at a relatively high amplitude that gradually decreases and wherein starting the session in a second mode of operation causes the vibration element to initially vibrate at a relatively low amplitude that gradually increases.

18 Claims, 3 Drawing Sheets

SYSTEMS AND METHODS FOR NEUROLOGIC VIBRATORY SENSE EVALUATION

BACKGROUND

Evaluation of a patient's ability to sense vibrations applied to the body is an important part of a neurological examination. In a current test, a 128 Hz tuning fork is struck against a rigid object to cause the tuning fork to vibrate and then it is placed against a body part of a patient under evaluation. For example, the tuning fork may be applied to the hallux, or "big toe," of the foot. The patient is asked to confirm that he or she can sense the vibrations. If the patient cannot sense any vibration, the tuning fork can be stuck again and applied to the malleolus of the ankle. If the vibrations still cannot be sensed, the test can be repeated on the tibial shaft or the anterior iliac crest. Assuming the patient can sense the vibrations at one of these locations, the patient is requested to indicate when the vibrations can no longer be sensed as the vibrations attenuate. The duration between the time at which the tuning fork is first applied and the time at which vibrations can no longer be sensed is indicative of the health of the patient's neurological system. A similar procedure can be used for testing the patient's fingers and hands.

While the above-described test provides the medical practitioner (e.g., physician, nurse, or physical therapist) with an idea of the functioning of the patient's neurological system, it has inherent disadvantages. First, there are no specific standards concerning the force with which the tuning fork is to be struck to start it vibrating. This force affects the amplitude of the vibrations generated by the tuning fork, with harder strikes generating higher vibration amplitudes that are easier to detect and softer strikes generating lower vibration amplitudes that are more difficult to sense. This variability can skew the results of the evaluation. For example, one practitioner may strike the tuning fork harder than a second practitioner and, as a consequence, longer sense durations may be observed by the first practitioner as compared to the second practitioner, even for the same patient.

In addition, there are also no specific standards as to how much force is to be used in applying the tuning fork to the patient's body. This can also skew the results. For example, if one practitioner presses the tuning fork against the patient's body with greater force than a second practitioner, the first practitioner may observe longer sense durations than the second practitioner as the vibrations are easier to detect when the tuning fork is applied with greater force.

The above variability associated with conventional vibratory sense evaluations is undesirable as it leads to inaccurate results. As such, it would be desirable to have systems and methods for neurologic vibratory sense evaluation that produce consistent results that do not vary as a function of the person conducting the evaluation.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
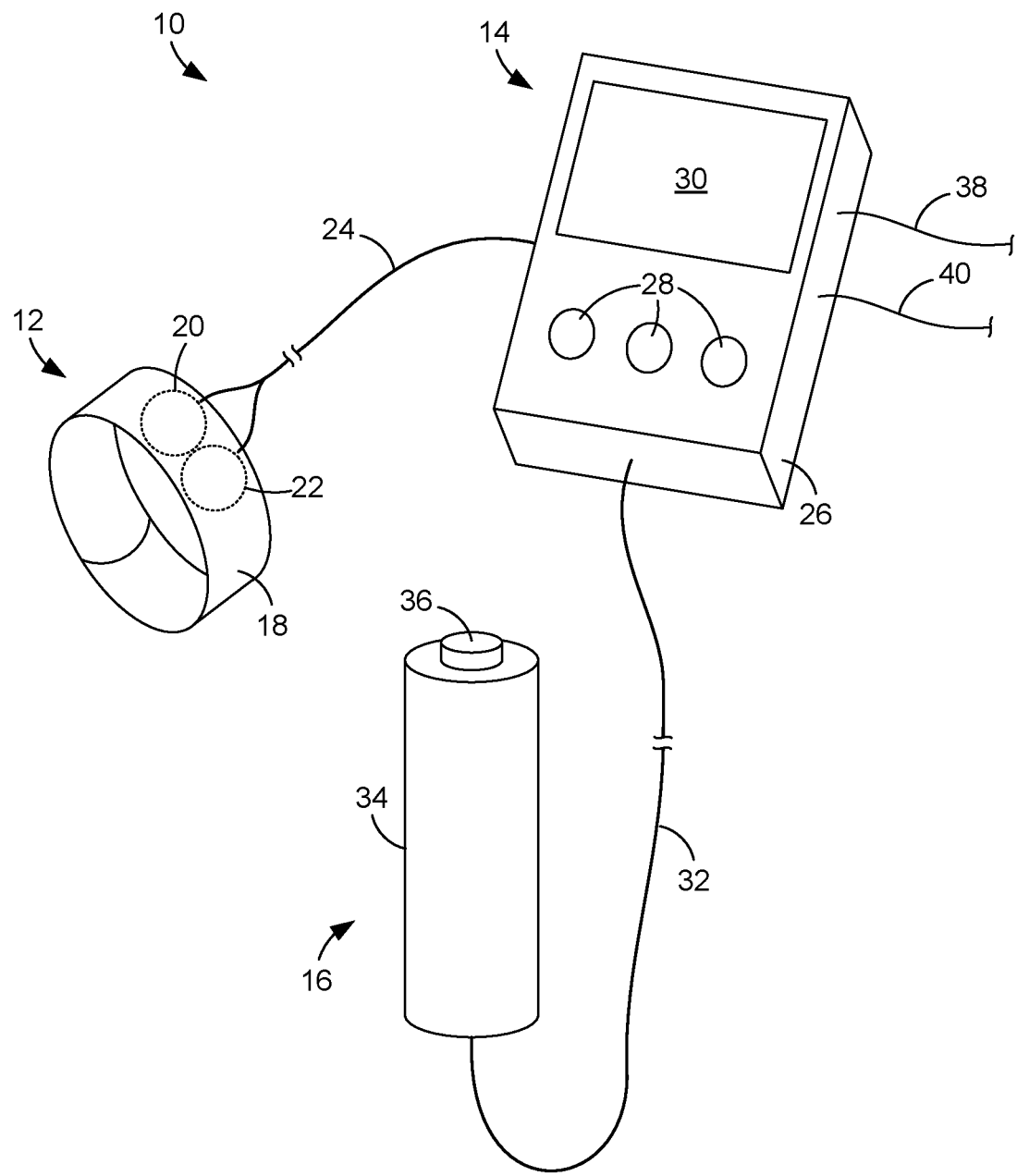
FIG. 1 is a schematic view of an embodiment of a system for neurologic vibratory sense evaluation.

As described above, it would be desirable to have systems and methods for neurologic vibratory sense evaluation that produce consistent results that do not vary as a function of the person conducting the evaluation. Examples of such systems and methods are disclosed herein. In one embodiment, a system for neurologic vibratory sense evaluation comprises a vibration element that can be applied to a patient's body with an amount of force within a predetermined range. The system further comprises a control module that precisely controls both the amplitude and frequency of the vibrations that are applied to the body with the vibration element. In a first mode of operation, relatively high amplitude vibrations are initially applied when the session is started and then the amplitude of the vibrations gradually decreases. In a second mode of operation, low amplitude vibrations (or no vibrations) are initially applied when the session is started and then the amplitude of the vibrations gradually increases. In both modes, the patient both starts and ends the session (indicating no longer sensing vibrations or initially sensing vibrations, depending on the mode) using a patient input device in electrical communication with the control module. In such a case, the medical practitioner conducting the evaluation cannot adversely influence the evaluation and the time at which the patient ends the session can be more precisely identified. As such, more accurate results can be obtained.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

The disclosed systems and methods enable more accurate vibratory sense evaluation by controlling the amplitude of the vibrations that are applied to the patient's body. In addition, the systems and methods can be used to control the force with which the vibrations are applied to the patient's body. When these parameters are controlled, more accurate results can be obtained that are not influenced by the individual conducting the evaluation. The results obtained using the systems and methods can be compared to those obtained using a tuning fork, if desired. In addition, with the disclosed systems and methods, new modes of evaluation are possible. For example, in addition to determining the time it takes for the patient to no longer sense the vibrations as the amplitude of the vibrations gradually attenuate, the time at which vibrations are first detected as the amplitude of the vibrations are gradually increased can also be determined. Furthermore, unlike with the conventional tuning-fork test, the amplitude of the vibrations at the time the patient no longer or first senses the vibrations can be determined. In some embodiments, the amplitude can be increased and decreased multiple times to more accurately identify the amplitude where sense perception diminishes.

FIG. 1 illustrates an example embodiment of a system 10 for neurologic vibratory sense evaluation. As shown in this figure, the system 10 generally comprises a vibration article 12, a control module 14, and a patient input device 16. The vibration article 12 is configured to attach to a patient's body and apply vibrations to the body to that can be used to evaluate the patient's neurological system. As described below, both the amplitude and the frequency of the vibrations applied by the vibration article 12 can be precisely controlled so that the same type of vibrations is applied to a patient's body each time an evaluation is performed. This avoids the variability that is possible when a tuning fork is used, as in prior art testing. In the example of FIG. 1, the vibration article 12 comprises a band 18 that can be wrapped around an appendage of the patient, such as a toe, a foot, an ankle, a leg, a finger, a hand, or an arm. The band 18 can be made of a flexible material, such as a fabric or polymeric material, and, in some embodiments, can be elastic. The band 18 can comprise a continuous (endless) band that can be slid over the patient appendage or can be a non-continuous band, in which case the band has opposed free ends that can be connected together with suitable fastening elements, such as hook and loop fasteners, snaps, a buckle, or the like.

As shown in FIG. 1, incorporated into the band 18 are a vibration element 20 and a force sensor 22. The vibration element 20 can comprise any device that is capable of generating vibrations of a desired amplitude and frequency. In some embodiments, the vibration element 20 is configured to generate vibrations of varying amplitude but constant frequency. Example devices that can be used as the vibration element 20 include a linear actuator, a piezoelectric element, a voice coil, or the like. The force sensor 22 is optional but, when provided, can be used to measure the force with which the band 18, and therefore the vibration element 20, is applied to the patient's body. By controlling this force, one can obtain more consistent results. Example devices that can be used as the force sensor 22 include a load cell, force transducers, a strain gauge, a piezoelectric sensor, or the like.

With further reference to FIG. 1, the vibration article 12 and, more particularly, the vibration element 20 and the force sensor 22, are placed in electrical communication with the control module 14 with a cable 24. The control module 14 is used to control operation of the vibration element 20 and to collect data from the force sensor 22. As shown in FIG. 1, the control module 14 comprises an outer housing 26 that supports a user interface that includes user input devices, such as one or more buttons 28, and a display 30, which can, for example, comprise a liquid crystal display (LCD). The buttons 28 can be used to control operation of the system 10 as a whole and the display 30 can be used to convey information collected by the system to the user (e.g., medical practitioner), as described below. An example configuration for the control module 14 is described below with reference to FIG. 2.

Referring again to FIG. 1, the patient input device 16 is also in electrical communication with the control module 14 through the use of a cable 32. In the illustrated example, the patient input device 16 comprises a generally cylindrical body 34 that is sized and configured to be held within a hand of the patient in similar manner to a microphone. At one end of body is a button 36 that can be depressed by the patient to register inputs. As described below, such inputs can initiate an evaluation session ("start") and terminate an evaluation session ("stop"). While a single button 36 is shown in FIG. 1, it will be appreciated that two buttons can be provided for purposes of starting and stopping a session, respectively. In such a case, one button may be green indicating "start," and the other button may be red, indicating "stop."

Also shown in FIG. 1 are two further cables 38 and 40 that extend from the control module 14. One of these cables 38 can be used to deliver power (e.g., voltage from a wall outlet) to the control module 14 and the other cable 40 can be used to transmit data to a separate computing device (not shown), such as a desktop computer, notebook computer, tablet computer, smart phone, or other device with computing capability.

Figure 2:
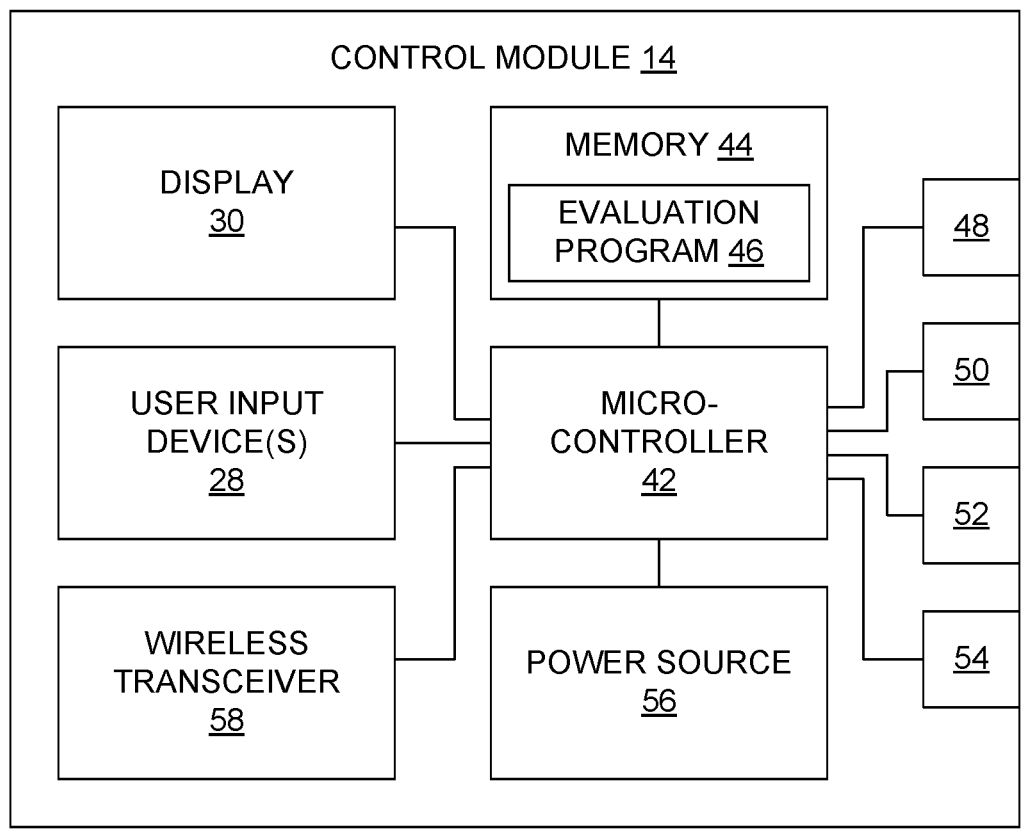
FIG. 2 is a block diagram of an embodiment of the architecture of a control module shown in FIG. 1.

FIG. 2 shows an example architecture for the control module 14. As shown in this figure, in addition to the user input devices (e.g., buttons) 28 and the display 30, the control module 14 can include a microcontroller 42 that controls the operation of the system 10 and memory 44 that stores an evaluation program 46 configured to receive inputs from the patient and calculate the durations of time between the start and stop of an evaluation session. In addition, the program 46 can be executed by the microcontroller 42 to control the amplitude and frequency of the vibrations generated by the vibration element 20 and to record the amplitude of the vibrations when the user inputs a "stop" command. While the memory 44 is shown as a separate component from the microcontroller 42, it will be appreciated that the memory can, in some embodiments, be integrated with the microcontroller.

Also shown in FIG. 2 are multiple electrical ports 48-54 that can be used for connection with the various cables 24, 32, 38, and 40 shown in FIG. 1. In addition, shown are an optional power source 56, such as a battery, which can be used to power the control module 14, and an optional wireless transceiver 58, which can be used to wirelessly transmit data to the separate computing device.

The system 10 can be used to conduct neurologic vibratory sense evaluations similar to those conducted using tuning forks, but with much greater accuracy. To conduct an evaluation, the control module 14 is powered on, for example, by pressing one of the buttons 28 (e.g., a "power" button). The vibration article 12 is then (or previously) applied to a body part of the patient. For example, the band 18 can be wrapped around the hallux of one of the patient's feet with the vibration element 20 positioned over the metatarsophalangeal joint. Because the control module 14 is powered on, measurements of the force sensor 22 are received by the control module 14. The control module 14 can display the measured force in the display 30 for the medical practitioner. With this information, the practitioner can adjust the band to ensure that the force is within some predetermined range. The magnitude of the force is not critical, as long as it is consistent in all testing. This way, more consistent results can be obtained. In some embodiments, the display 30 can notify the practitioner when the measured force is outside of the predetermined range so that the practitioner can make the necessary adjustments. Such a notification can, for example, comprise a flashing message or other obvious indication. In other embodiments, an evaluation session can only be performed if the force is within a predetermined range to avoid erroneous assessments. In such a case, the control module 14 can, for example, ignore inputs intended to start the session until the force reading is within the range.

Once the vibration article 12 has been applied to the patient's body with a proper amount of force, an evaluation session can be conducted. In some embodiments, the session is started and stopped by the patient. For example, if the user input device 16 comprises a single button 36, the patient can start the session by pressing the button a first time and can end the session by pressing the button a second time. The nature of the session depends upon the mode in which the system 10 is operating, for example, using a mode button provided on the control module 14. In a first mode, relatively high amplitude vibrations are initially applied by the vibration element 20 when the session is started and then the amplitude of the vibrations gradually decreases. In some embodiments, the amplitude decreases at a decay rate that emulates the rate at which the vibration of a tuning fork decays. The vibrations can be controlled to have a constant frequency, such as 128 Hz, just as in the tuning-fork test. In such a mode, the patient can indicate when the vibrations are no longer sensed, again, as in the tuning-fork test.

In a second mode, low amplitude vibrations (or no vibrations) are initially applied by the vibration element 20 when the session is started and then the amplitude of the vibrations gradually increases. The amplitude can, for example, be increased at a rate that is the inverse of the decay rate used in the first mode. Again, the vibrations can be controlled to have a constant frequency, such as 128 Hz. In the second mode, the patient can indicate when the vibrations are first sensed. This additional mode is not practiced in the prior art but may be useful as the points at which the vibrations are no longer sensed and first sensed may be different due to hysteresis. In some embodiments, the two data points can be considered independently or averaged together, and can be repeated for greater accuracy.

In either mode of operation, the patient starts the evaluation session by pressing a button and ends the session by pressing the button again (or pressing a separate button). The control module 14 tracks the duration of time between the start and end of the session, and this duration can be displayed in the display 30, stored within memory 44, and/or transmitted to the separate computing device. In addition, the control module 14 identifies the amplitude of the vibrations at the time the patient presses the button to signal when the vibrations are no longer or first sensed, depending upon the mode of operation. This information can also be displayed in the display 30, stored within memory 44, and/or transmitted to the separate computing device. In some embodiments, multiple sessions can be conducted in each mode and the results can be separately averaged to obtain Mode 1 averages and Mode 2 averages. These averages can also be computed by the control module 14 and can also be displayed in the display 30, stored within memory 44, and/or transmitted to the separate computing device.

Figure 3:
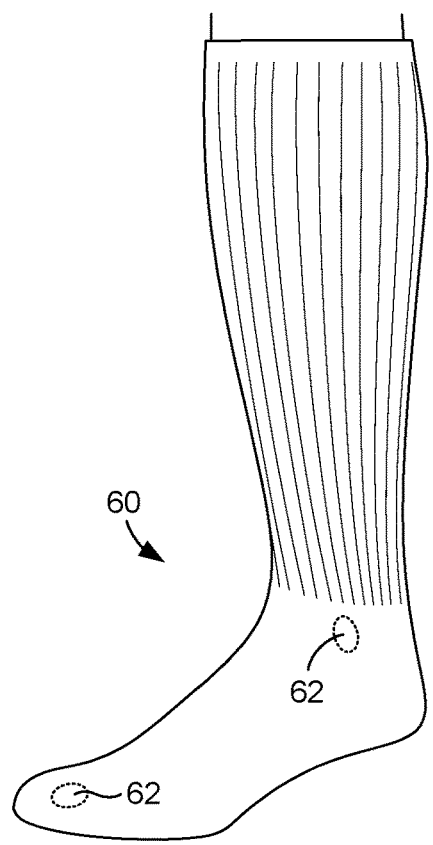
FIG. 3 is a schematic view of a first embodiment of a vibration article that can be used in the system of FIG. 1.
Figure 4:
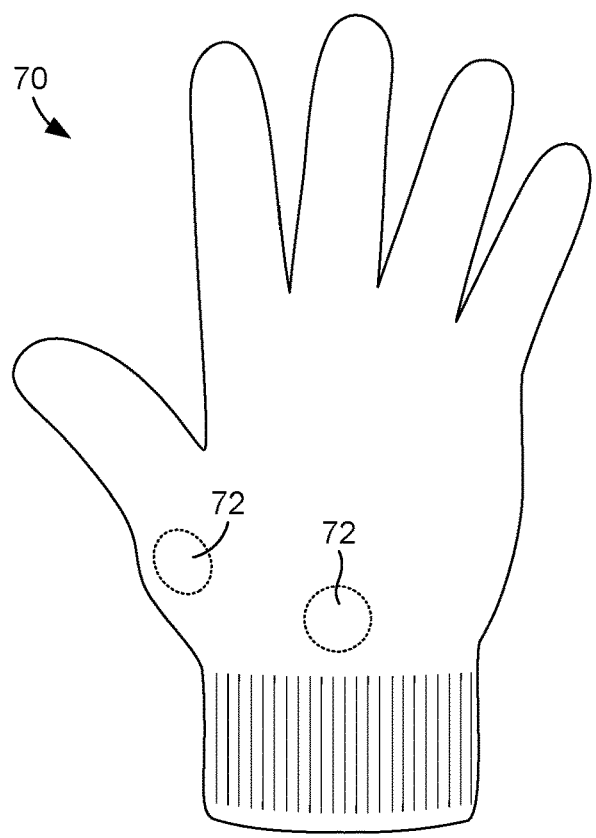
FIG. 4 is a schematic view of a second embodiment of a vibration article that can be used in the system of FIG. 1.

While the vibration article 12 shown in FIG. 1 takes the form of a band 18, it is noted that the vibration article can have other configurations. FIGS. 3 and 4 show two examples. In FIG. 3, the vibration article is configured as a sock 60 that includes one or more vibration elements 62 that are integrated into the material of the sock. The location of the vibration elements 62 within the sock 60 are selected so as to position the elements at the correct locations on the patient's body when the sock is worn by the patient. In FIG. 4, the vibration article is configured as a glove 70 that also includes one or more vibration elements 72 that are integrated into the material of the glove. The location of the vibration elements 62 within the glove 72 are likewise selected so as to position the elements at the correct locations on the patient's body. Notably, the sock 60 and glove 70 are just two further examples of vibration articles that can be worn by a patient. Another example is sleeves that can be applied to the legs or arms. Generally speaking, the vibration article can take the form of any article that can be attached to or worn by the patient.

It is noted that the system for neurologic vibratory sense evaluation can further include components that are used to conduct other evaluations relevant to a patient's neurological system. For example, appropriate sensors can be integrated into the sock 60 to perform a heel-to-shin test or into the glove 70 to perform a finger-to-thumb crease test, if desired.

The invention claimed is:

1. A system for neurologic vibratory sense evaluation, the system comprising:
   a flexible vibration article configured to be worn on a body part of a patient under evaluation, the vibration article comprising a vibration element configured to vibrate against the body part and a force sensor configured to measure a force with which the article is pressed against the body part;
   a control module comprising a microcontroller, memory that stores an evaluation program that can be executed by the microcontroller, a user interface configured to receive user commands, and a display configured to communicate information about evaluation sessions to the user, wherein the evaluation program is configured to control the vibration element in a first mode of operation to initially vibrate at a relatively high amplitude that gradually decreases when an evaluation session is started and to control the vibration element in a second mode of operation to initially vibrate at a relatively low amplitude that gradually increases when an evaluation session is started, the vibrations generated by the vibration element having a constant frequency of 128 Hz, the evaluation program further being configured to calculate a duration of time between a start and a stop of the evaluation session and to identify an amplitude of the vibrations at the moment the session is stopped; and
   a patient input device configured to enable a patient to start and stop the evaluation sessions, wherein the input device comprises a member configured to be held in the patient's hand and at least one button configured to be pressed by the patient to start and stop the evaluation session.

2. A system for neurologic vibratory sense evaluation, the system comprising:
   a vibration article configured to attach to a body part of a patient under evaluation, the vibration article comprising a vibration element configured to vibrate against the body part;
   a control module including an evaluation program configured to control both an amplitude of vibrations generated by the vibration element; and
   a patient input device configured to enable a patient to start and stop an evaluation session, wherein starting the session in a first mode of operation causes the control module to execute the evaluation program and automatically control the vibration element to initially vibrate at a relatively high amplitude that gradually decreases.

3. The system of claim 2, wherein the vibration article comprises a flexible strap configured to wrap around an appendage of the patient's body.

4. The system of claim 2, wherein the vibration article comprises an article of clothing configured to be worn by the patient.

5. The system of claim 4, wherein the article of clothing is a sock, a glove, or a sleeve.

6. The system of claim 2, wherein the control module comprises a microcontroller and memory that stores an evaluation program configured to calculate a duration of time between the start and the stop of the evaluation session, the evaluation program further being configured to identify an amplitude of the vibrations at the moment the session is stopped by the patient.

7. The system of claim 6, wherein the control module further comprises a user interface configured to receive user commands and a display configured to communicate information about the evaluation session to the user.

8. The system of claim 2, wherein starting the evaluation session in a second mode of operation causes the control module to execute the evaluation program and automatically control the vibration element to initially vibrate at a relatively low amplitude that gradually increases.

9. The system of claim 8, wherein the vibrations have a constant frequency of 128 Hz in both modes.

10. The system of claim 2, wherein the user input device comprises a member configured to be held in the patient's hand and at least one button configured to be pressed to start the evaluation session.

11. The system of claim 2, wherein the vibration article further comprises a force sensor in electrical communication with the control module configured to measure a force with which the article is attached to the patient.

12. A method for evaluating a patient neurological system, the method comprising:
applying a vibration element to a body part of a patient under evaluation, the vibration element being configured to vibrate against the body part;
measuring a force with which the vibration element is applied to the body part;
operating the vibration element in a first mode in which relatively high amplitude vibrations are initially applied to the body part and the vibrations thereafter gradually decrease, the vibrations having a constant frequency;
determining a duration of time between the initial application of the vibrations and a time at which the patient can no longer sense the vibrations; and
determining the amplitude of the vibrations at the moment that the patient can no longer sense the vibrations.

13. The method of claim 12, wherein applying a vibration element comprises attaching a vibration article that supports the vibration element to the body part.

14. The method of claim 13, wherein measuring a force comprises measuring the force with a force sensor that is also supported by the vibration article.

15. The method of claim 12, wherein determining a duration of time and determining the amplitude comprises determining these parameters using a control module that controls the vibration element.

16. The method of claim 15, wherein determining a duration of time comprises determining when the patient starts the evaluation session and when the patient stops the evaluation session based upon inputs received from the patient with a patient input device.

17. The method of claim 12, further comprising operating the vibration element in a second mode in which relatively low amplitude vibrations are initially applied to the body part and the vibrations thereafter gradually increase, the vibrations having a constant frequency.

18. The method of claim 12, wherein the vibrations have a frequency of 128 Hz.

* * * * *

UNITED STATES PATENT AND TRADEMARK OFFICE
CERTIFICATE OF CORRECTION

PATENT NO.         : 11,083,373 B1                                    Page 1 of 1
APPLICATION NO.    : 16/359343
DATED              : August 10, 2021
INVENTOR(S)        : Kyle Brandon Reed et al.

It is certified that error appears in the above-identified patent and that said Letters Patent is hereby corrected as shown below:

In the Claims

Column 6, Claim 2, Line 47, "control both an" should be --control an--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*